United States Patent [19]
Ueda

[11] Patent Number: 4,565,423
[45] Date of Patent: Jan. 21, 1986

[54] CONNECTING DEVICE FOR AN ENDOSCOPE

[75] Inventor: Yasuhiro Ueda, Tokyo, Japan

[73] Assignee: Olympus Optical Co., Ltd., Tokyo, Japan

[21] Appl. No.: 724,939

[22] Filed: Apr. 19, 1985

Related U.S. Application Data

[63] Continuation of Ser. No. 463,673, Feb. 4, 1983, abandoned.

[30] Foreign Application Priority Data

Feb. 8, 1982 [JP] Japan .................................. 57-18595
Feb. 8, 1982 [JP] Japan .................................. 57-18597

[51] Int. Cl.⁴ .............................................. G02B 27/14
[52] U.S. Cl. .................................... 350/171; 350/173; 128/6
[58] Field of Search ........................ 350/171, 502, 506; 128/4, 6, 172, 173, 174

[56] References Cited

U.S. PATENT DOCUMENTS 3,623,807 11/1971 Gabler et al. .......................... 350/502
4,283,115 8/1981 Fraissl .
4,344,667 8/1982 Wooff .................................. 350/502

FOREIGN PATENT DOCUMENTS 0036626 9/1981 European Pat. Off. .
1941110 2/1971 Fed. Rep. of Germany .
2415773 10/1975 Fed. Rep. of Germany .
2927959 1/1980 Fed. Rep. of Germany .
56-80102 6/1981 Japan .
56-151018 11/1981 Japan .

Primary Examiner—John K. Corbin
Assistant Examiner—P. M. Dzierzynski

[57] ABSTRACT

A connecting device includes a cylindrical body to both ends of which are connected an endoscope and a television camera and from which a light guide provided with an eyepiece section at its one end for connecting a steal camera is extended. In the cylindrical body is provided a support in which first and second prisms having different light splitting ratios are movably provided to selectively face the other end of the light guide.

8 Claims, 15 Drawing Figures

CONNECTING DEVICE FOR AN ENDOSCOPE

This application is a continuation of application Ser. No. 463,673, filed Feb. 4, 1983 now abandoned.

BACKGROUND OF THE INVENTION

This invention relates to a connecting device for connecting an endoscope and a television camera.

For examining the body cavity using an endoscope, there are various ways of examination such as televising the endoscopic image, photographing the image or watching the image with the eye. These ways of examination are selectively used depending upon the situation. For the endoscopic examination, it is accordingly important to be able to readily and quickly switch the various ways of examination noted above.

In order to permit endoscopic examination in a plurality of different ways, the eyepiece section of the endoscope is usually provided with a connector, which permits connection of a television camera and also examination with the eye. With this connector, however, for photographing an endoscopically examined image it is necessary to first remove the connector from the eyepiece section of the endoscope and then install a still camera on the eyepiece section. This operation cannot be done momentarily. Besides, it is liable to loose the location to be photographed while removing the connector.

To overcome these inconveniences, it has been proposed to provide the connector with another eyepiece section, on which the still camera can be installed so that it can be used both for photographing and examination with the eye.

However, when providing the connector with an eyepiece section, a prism provided as a light splitter in the connector must have such a light splitting ratio that more light is led to the side of the television camera than to the side of the eyepiece section because the light sensitivity of the usual television camera is inferior. Therefore, although there is no trouble for the examination with the eye through the eyepiece section, with the still camera mounted on the eyepiece section the light intensity that is obtainable is insufficient for the photographing. That is, reliable photographing cannot be obtained by merely providing the connector with an eyepiece section, on which the still camera can be mounted.

SUMMARY OF THE INVENTION

An object of the invention is to provide a connecting device for an endoscope, which couples together an endoscope and a television camera both mechanically and optically and can also lead light from the endoscope to the television camera and a still camera mounted on its eyepiece section with a different light splitting ratio than that when the still camera is not mounted on the eyepiece section.

In the connecting device according to the invention, at least two light splitters such as prisms or half mirrors having different light splitting ratios are used such that they can be selectively brought to an operative position to provide the best light splitting ratio.

BRIEF DESCRIPTION OF THE DRAWINGS

FIGS. 1 to 5 show a first embodiment of a connecting device for an endoscope according to the invention, in which

FIGS. 8 to 12 show a third embodiment of a connecting device for an endoscope according to the invention, in which

DETAILED DESCRIPTION OF THE PREFERRED EMBODIMENTS

Now, an embodiment of the connecting device for an endoscope according to the invention will be described with reference to FIGS. 1 to 5.

Figure 1:
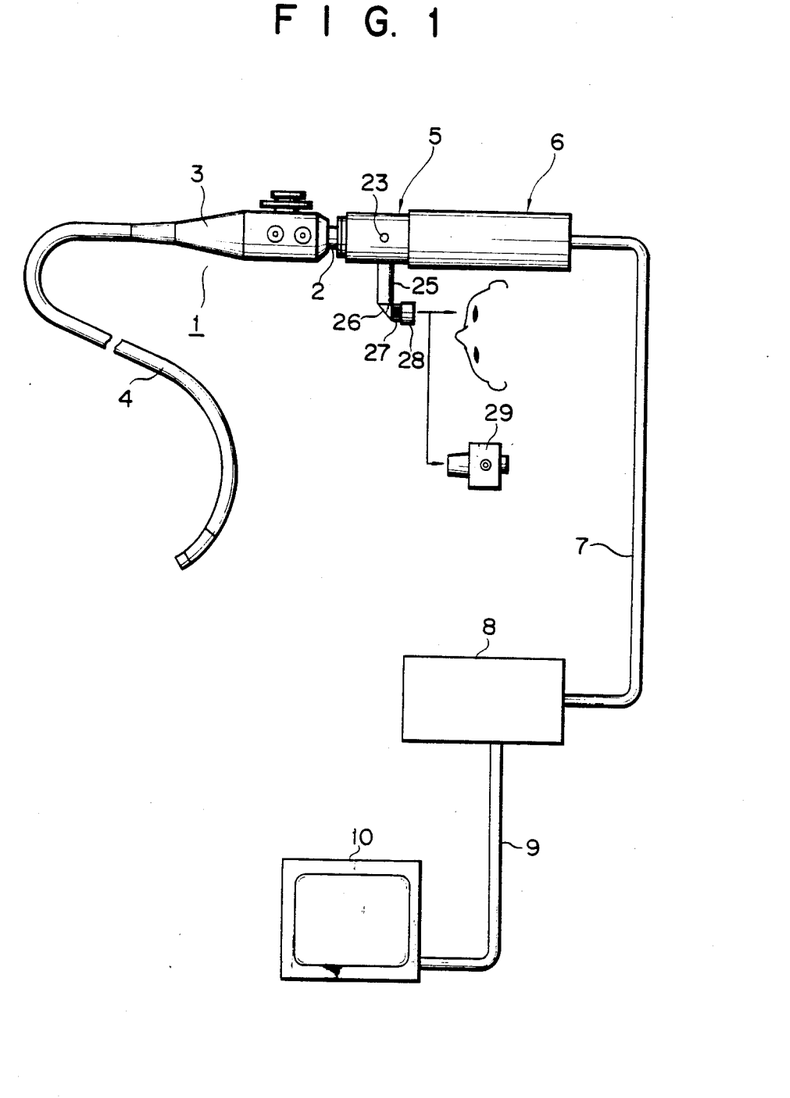
FIG. 1 is a view schematically showing the positional relation among an endoscope, a television camera, a still camera and a connecting device.

Referring now to FIG. 1, reference numeral 1 generally designates an endoscope. The endoscope 1 is of a well-known type comprising an eyepiece section 2, an operating section 3 provided adjacent to the eyepiece section 2 and an insert section 4 extending from the operating section 3 and to be inserted into the patient's body cavity. A television camera 6 which is well known in the art may be connected to the eyepiece section 2 of the endoscope 1 on a first optical axis through a connecting device 5. The television camera 6 is connected to a control unit 8 through a first cable 7. The control unit 8 is connected to a television monitor 10 through a second cable 9. An electric signal obtained from the television camera 6 is amplified in the control unit 8 and then processed to obtain a video signal. A composite video signal is obtained by combining the video signal with synchronous signals, and it is supplied to the television monitor 10 to reproduce the televised image on the television monitor 10.

Figure 2:
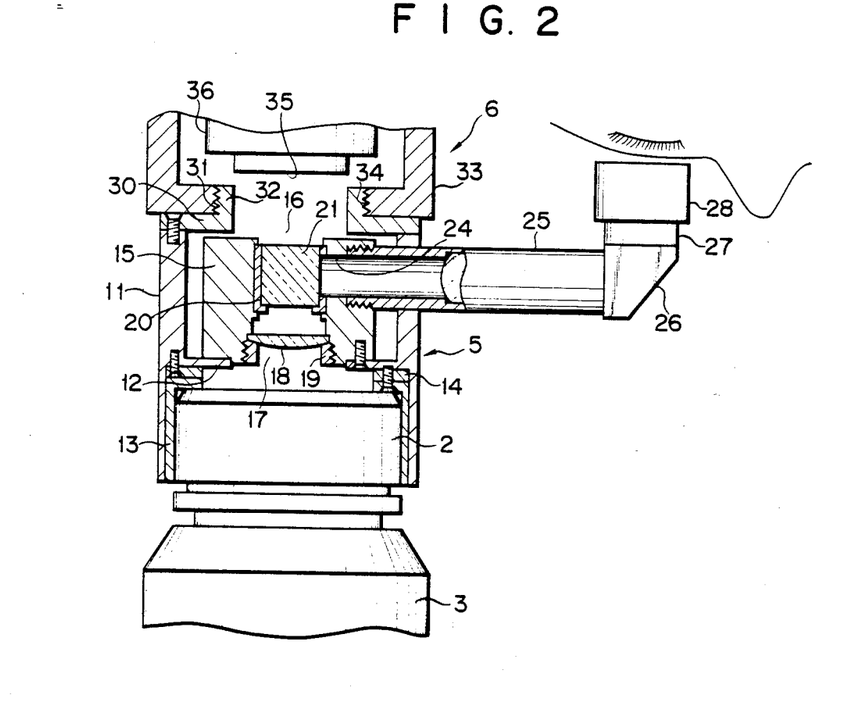
FIG. 2 is a longitudinal sectional view of the connecting device.
Figure 3:
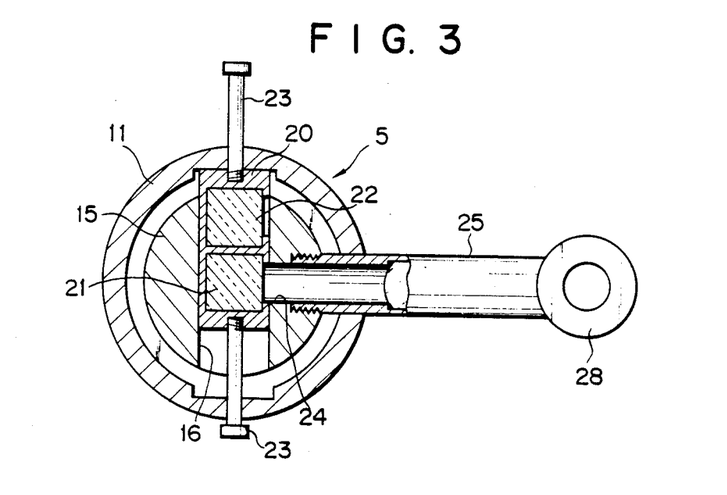
FIG. 3 is a transversal sectional view of the connecting device.

As shown in FIGS. 2 and 3, the connecting device 5 comprises a cylindrical body 11, which has an annular inner projection 12 formed in its axially intermediate position. The body 11 accommodates a mounting cylinder 13 mounted in its portion adjacent to one end, lower end in FIG. 2. The mounting cylinder 13 is fitted on the eyepiece section 2 of the endoscope 1. Its upper annular end is secured by screws to the annular inner projection 12 noted above via a spacer 14. A cylindrical support 15 is disposed in the body 11, and is secured by screws to the upper surface of the annular inner projection 12. The support 15 has a mounting groove 16 formed in its upper surface. The mounting groove 16 crosses the support 15 in the diametrical direction thereof. It has a rectangular sectional profile and is open at the opposite ends from the peripheral surface of the support. The support 15 also has a circular hole 17 coaxially extending through its lower end portion. The circular hole 17 communicates at its upper end with a central portion of the mounting groove 16 and is open at the lower end. A convex lens 18 is disposed in the hole 17 and coaxially retained therein by a retainer ring 19. A slidable prism holder 20 is disposed in the mounting groove 16 for movement in the diametrical direction of the support 15 along the mounting groove. The prism holder 20 has a box-like shape open at the upper and lower ends, and it carries a first prism 21 and a second prism 22, these prisms being disposed in it and secured to it. The first and second prisms 21 and 22 have different light splitting ratios. In this embodiment, the first prism 21 has such a light splitting ratio of 7:3, that is, it leads 70% of light from the endoscope 1 to the side of the television camera 6 and leads 30% of light to the side of an eyepiece section to be described later, while the second prism 22 has a light splitting ratio of 5:5, that is, it leads 50% of incident light to the side of the television camera 6 and also leads the other 50% of light to the side of the eyepiece section. The peripheral wall of the body 11 is formed with a pair of diametrically opposed through holes extending in the same direction as the mounting groove 16. Operating rods 23 penetrate these holes. The stems of the operating rods 23 project from the outer periphery of the body 11 and can be operated with fingers. The ends of the operating rods extending in the body 11 are secured to the opposite ends of the movable prism holder 20. The prism holder 20 may be moved along the mounting groove 16 by pushing and pulling the operating rods. The prism holder 20 may be moved to one of two selectable positions, i.e., a first position in which the first prism 21 faces the lens 18 and a second position in which the second prism 22 faces the lens 18. A click mechanism is preferably provided between the movable prism holder and body so that the prism holder 20 may be assuredly set to the first and second positions. One side wall of the movable prism holder 20 is provided with a pair of holes facing the side of the respective prisms 21 and 22 from which light emerges. The periphery of the support 15 is formed with a radial hole extending at right angles to the groove 16. One end portion of a light guide 25 having a second optical axis is inserted in this hole of the support 15 and is secured to the same. When the movable prism holder 20 is in the first position, the end of the light guide 25 faces the corresponding side of the first prism through the associated hole formed in the movable prism holder 20. When the prism holder 20 is in the second position, the end of the light guide 25 faces corresponding side of the second prism through the associated hole in the prism holder 20. The other end of the light guide 25 projects from the outer periphery of the body 11, and is provided with a connecting section 26, in which the direction of light led through the light guide is changed by right angles. An eyepiece section 28 is provided on the connecting section 26. The eyepiece section includes a dioptar lens 27 for focusing. To the eyepiece section 28 is to be connected a still camera 35.

A ring-like connecting member 30 is coaxially connected to the other end of the body 11 of the connecting device 5. The connecting member 30 has a central cylindrical portion 32 with the outer periphery thereof formed with a male thread 31. The television camera 6 has a cylindrical casing 33 having one end formed with a threaded hole 34, which is screwed on the cylindrical portion 32. An image pick-up tube 36 is accommodated in the casing 33 of the television camera 6 such that its image pick-up surface 35 faces or is aligned to the lens 18 in the connecting device 5 through the threaded hole 34 and the prism (i.e, the first or second prism 21 or 22).

The operation of the connecting device 5 having the above construction will now be described.

When, the body cavity is to be examined with the eye through the endoscope while televising the examined image on the television monitor 10, the movable prism holder 20 is moved to the first position shown in FIG. 3 by pulling or pushing the operating rods 23. Thus, the first prism 21 having the light splitting ratio of 7:3 is brought to a position to face the lens 18 and the light guide 25. In this case, 70% of the light entering the connecting device 5 through the eyepiece section 2 of the endoscope 1 is transmitted through the first prism 21 to be incident on the image pick-up tube 36 of the television camera 6, while the remaining 30% of light is led through the prism 21, light guide 25 and connecting section 26 to the eyepiece section 28 of the connecting device 5. Since the intensity of light incident on the television camera 6 at this time is sufficient, the image of the body cavity examined can be satisfactorily televised on the television monitor 10. Meanwhile, only 30% of light incident on the connecting device 5 is led to the eyepiece section 28. Even with this order of light intensity, the examination with the eye can be done satisfactorily.

Figure 4:
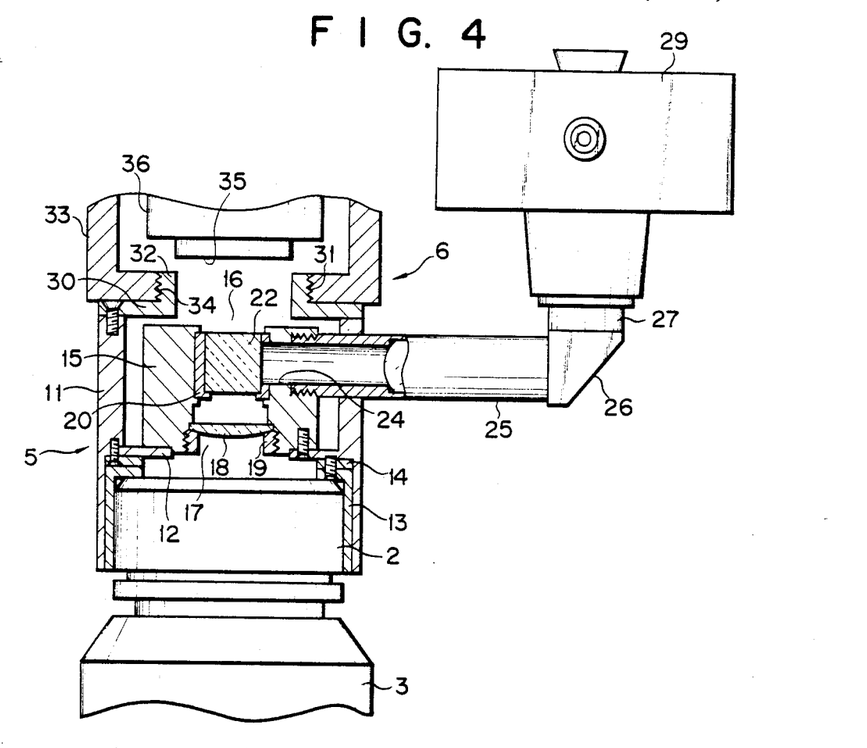
FIG. 4 is a view similar to FIG. 2 but showing the device in a different operating state.
Figure 5:
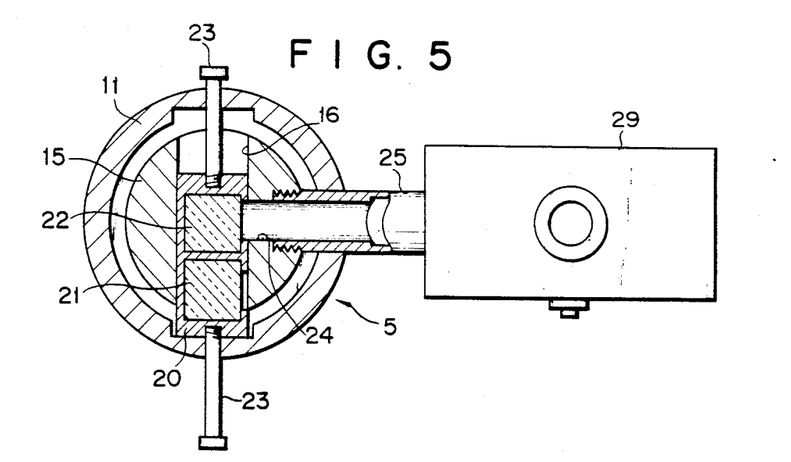
FIG. 5 is a view similar to FIG. 3 but showing the device in a different operating state.

When the body cavity image examined through the endoscope 1 is to be televised, a still camera 29 is mounted on the eyepiece section 28 of the connecting device 5, while the movable prism holder 20 is moved to the second position as shown in FIGS. 4 and 5. Thus, the second prism 22 having the light splitting ratio of 5:5 is brought to a position to face the lens 18 and light guide 25. Thus, of the light entering from the eyepiece section 2 of the endoscope into the connecting device, 50% is directed by the second prism 22 to the image pick-up tube 36 of the television camera, while the remaining 50% is led to the eyepiece section 28 of the connecting device 5. In this case, more light than in the case of the examination with the eye is led to the eyepiece section 28, so that the photographing can be done satisfactorily with the still camera 29 mounted on the eyepiece section 28. Meanwhile, the intensity of light incident on the image pick-up tube 36 of the television camera 6 is reduced compared to the case of examination with the eye. However, the body cavity image examined can be televised on the television monitor 10 satisfactorily for determining the location to be photographed with the still camera 29.

As has been shown, with the connecting device 5 of this embodiment the intensity of light incident on the eyepiece section can be increased by merely switching the first and second prisms 21 and 22 contained in the connecting device 5, so that photographing can be done satisfactorily by mounting the still camera 29 on the eyepiece section 28.

Now, different embodiments will be described with reference to the drawings. The same or equivalent parts as those in the preceding embodiment are designated by like reference numerals, and their detailed description is omitted.

Figure 6:
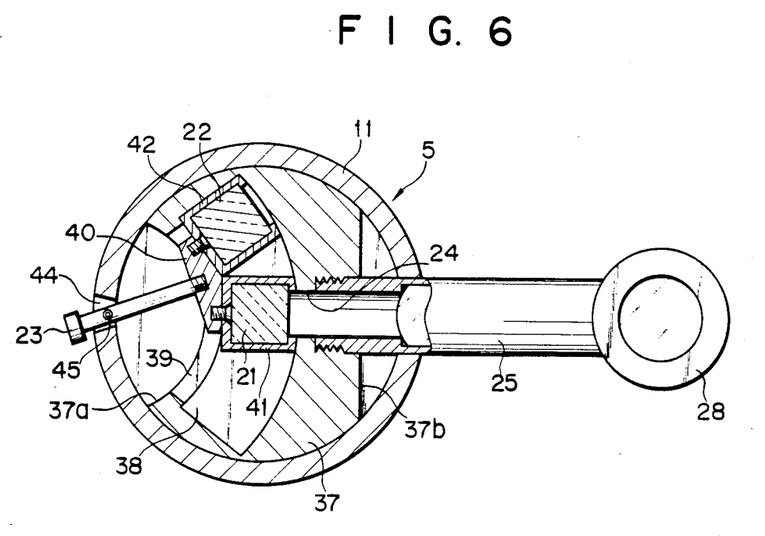
FIGS. 6 and 7 are sectional views showing a second embodiment of a connecting device for an endoscope according to the invention in different operating states.
Figure 7:
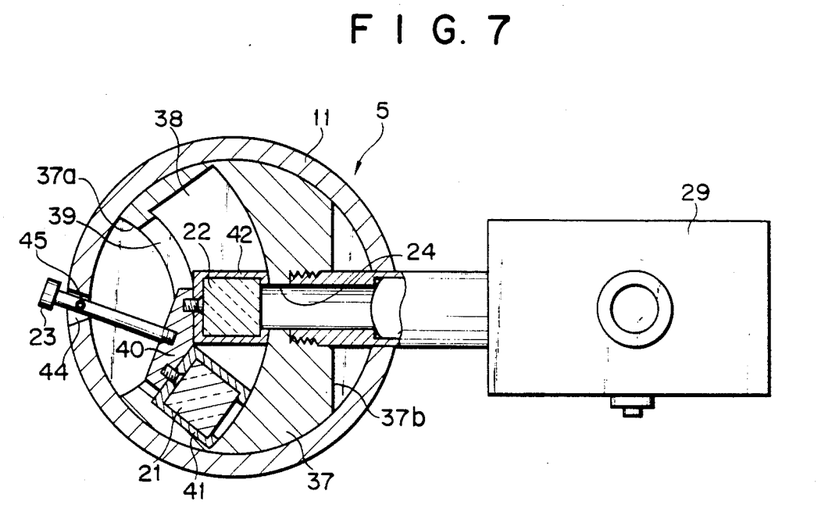
Figure 8:
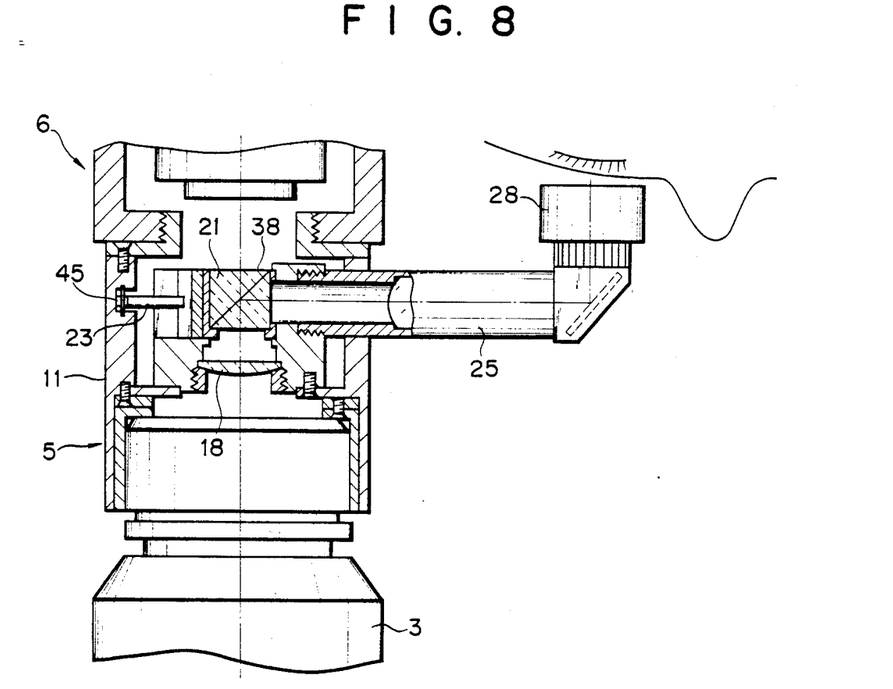
FIG. 8 is a longitudinal sectional view of the connecting device.

FIGS. 6 and 7 show a second embodiment. Here, a support 37 provided in the cylindrical body 11 of the connecting device 5 has an arcular profile surface 37a formed on one side and also has a plane surface 37b formed on the other side. The support 37 also has an arcular mounting groove 38 formed in its upper surface. The arcular mounting groove 38 is concentric with the arcular surface 37a. The support 37 further has a horizontal guide opening 39 or window formed in the arcular surface 37a and communicating with the mounting groove 38. A movable prism holder 40 is disposed for movement in the horizontal plane along the guide opening 39. The prism holder 40 has two inclining surfaces which face the groove 38 and which meet at their edges, thus forming a ridge. First and second support frames 41 and 42 are secured to the respective inclined surfaces of the prism holder 40. These support frames are movable along the mounting groove 38. These support frames 41 and 42 carry first and second prisms 21 and 22 secured to them respectively. Each support frame is open at the upper and lower ends, and on its side opposite the movable prism holder 40 is formed with a hole which can be communicated with a light guide 25.

An operating rod 23 is secured at one end to the movable prism holder 40. The other end of the operating rod 23 projects outwardly from the outer periphery of the body 11 through a through hole 44 formed therein. A portion of the operating rod 23 extending in the through hole 44 is pivoted by a pin 45 to the body 11 so that the operating rod 23 is rotatable about the pin 45 in a horizontal plane. The pin 45 is so disposed that it is a center of the arc mounting groove 38. The first and second prisms 21 and 22 thus may be moved with the respective support frames 41 and 42 along the mounting groove 38 between a first and a second position by operating the operating rod 23. Thus the examination of a body cavity image with the eye may be done satisfactorily when the first prism 21 is in its position facing the light guide 25 as shown in FIG. 6, while the photographing of the image may be done with a still camera satisfactorily when the second prism 22 is in the position facing the light guide 25.

Figure 9:
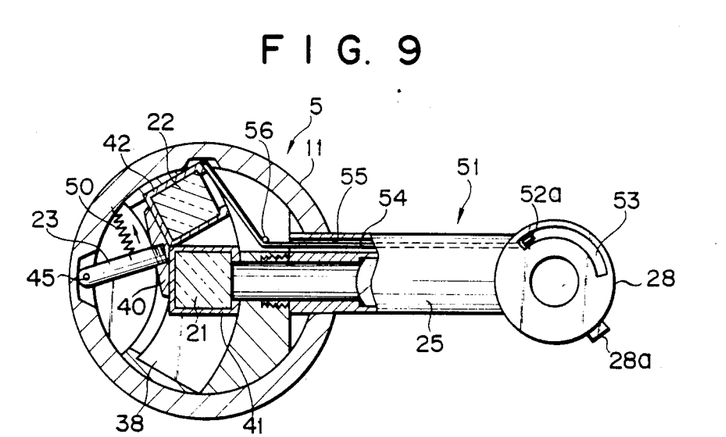
FIG. 9 is a transversal sectional view of the same device.

FIGS. 8 to 13 show a third embodiment of the connecting device. Here, the operating rod 23 which is secured at one end to the movable prism holder 40 carrying the support frames 41 and 42 does not project outwardly from the body 11 at the other end. More particularly, the other end is received in a recess formed in the inner wall of the body 11 and is pivoted thereto by the pin 45. A tension coil spring 50 is stretched between an intermediate portion of the operating rod 23 and the inner peripheral wall of the body 11. The operating rod 23 is thus biased in the counterclockwise direction as shown in FIG. 9. Normally, i.e., without the still camera 29 mounted on the eyepiece section 28, the movable prism holder 40 is held at its first position at which the first prism 21 faces the light guide 25.

Figure 10:
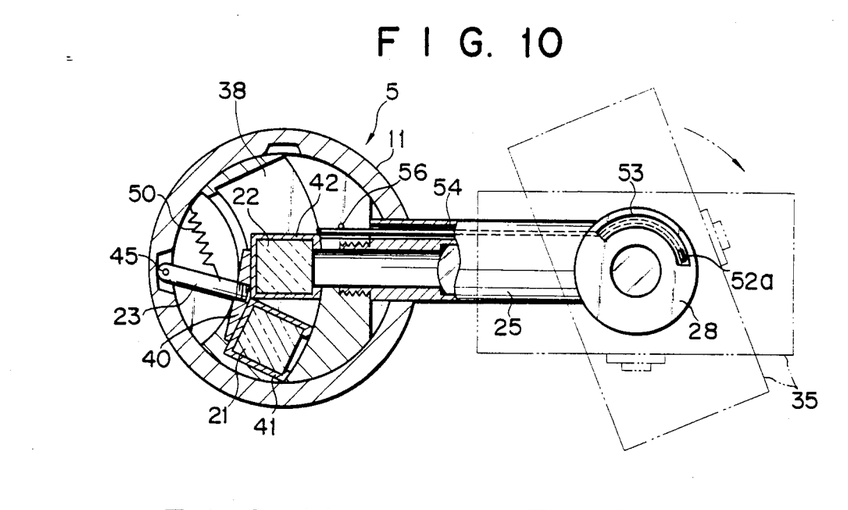
FIG. 10 is a view similar to FIG. 9 but showing the device in a different operating state.

As shown in FIG. 10, this embodiment of the connecting device includes a drive mechanism 51 which automatically brings the movable prism holder 40 to the second position, in which the second prism 22 faces the light guide 25, when the still camera 29 is mounted on the eyepiece section 28. This mechanism will now be described in detail.

For instance, a bayonet mechanism is provided between the eyepiece section 28 and still camera 29, and functions to mount and demount the still camera 29 with respect to the eyepiece section 28. In this embodiment this bayonet mechanism constructed by an engagement projection 28a (FIG. 9) projecting from the periphery of the eyepiece section 28 and an L-shaped slot 29b (FIG. 13) formed in a mount 29a of the still camera 29.

Figure 13:
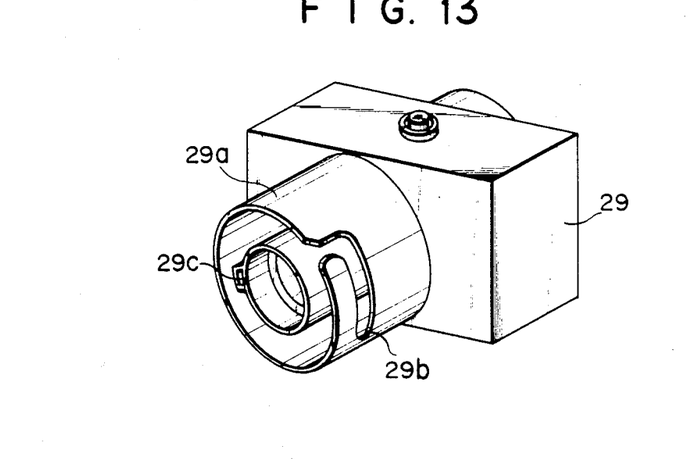
FIG. 13 is a perspective view showing an example of the still camera used with the third embodiment of the connecting device.

The engagement projection 28a can be engaged in the L-shaped slot 29b.

Figure 11:
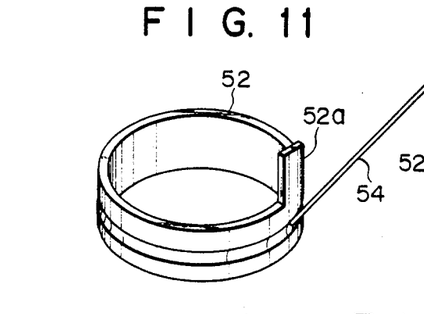
FIGS. 11 and 12 are fragmentary perspective views showing a drive mechanism in different operating states.
Figure 12:
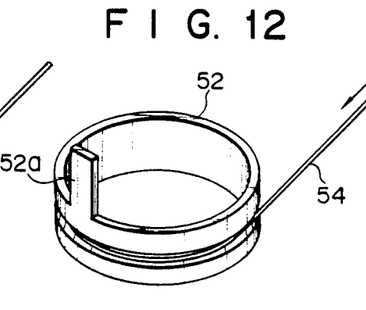

The eyepiece section 28 includes a rotary ring 52 therein as shown in FIGS. 11 and 12. The rotary ring 52 has an engagement projection 52a, which projects through an arcuate slot 53 formed in the top of the eyepiece section 28. The outer periphery of the rotary ring 52 is formed with an annular groove, and an end of a wire 54 is secured to the annular groove. The wire 54 is led from this rotary ring into the body 11 through a guide path 55 formed to extend substantially horizontally along the peripheral wall of the light guide 25. In the body 11, the wire 54 is passed turned a pin 56 projecting from the bottom of a recess formed in an upper portion of the support 15. The other end of the wire 54 is secured to the side wall of the second support frame 42 opposite the first support frame 41.

As shown in FIG. 13, the mount 29a of the still camera 29 is formed with an engagement section 29c. The engagement projection 52a of the rotary ring 52 is received or engaged in the engagement section 29c when the still camera 29 is connected to the eyepiece section 28. At this time, the engagement projection 28a of the eyepiece section 28 is also received in the engagement slot 29b. Then, by turning the still camera 29 in the counterclockwise direction as shown by an arrow in FIG. 10, the rotary ring 52 is also rotated in the same direction via the engagement section 29c and engagement projection 52a, and at the same time the engagement projection 28a is moved along the slot 29b. By the latter operation, the still camera 29 is locked to the eyepiece section 28, and by the former operation the wire 54 is taken up on the outer periphery of the rotary ring 52 so that the second support frame 42 is pulled by the wire 54. The movable prism holder 40 supporting the second support frame 42 is thus rotated about the pin 45 in the clockwise direction in FIG. 9 against the biasing force of the spring 50. When the still camera is fully turned, the second prism 22 supported by the support frame 42 is brought to the position to face the lens 18 and light guide 25.

As has been shown, in this embodiment of the connecting device the switching of the first and second prisms may be done automatically by the mechanical drive mechanism with the mounting and demounting of the still camera.

Figure 14:
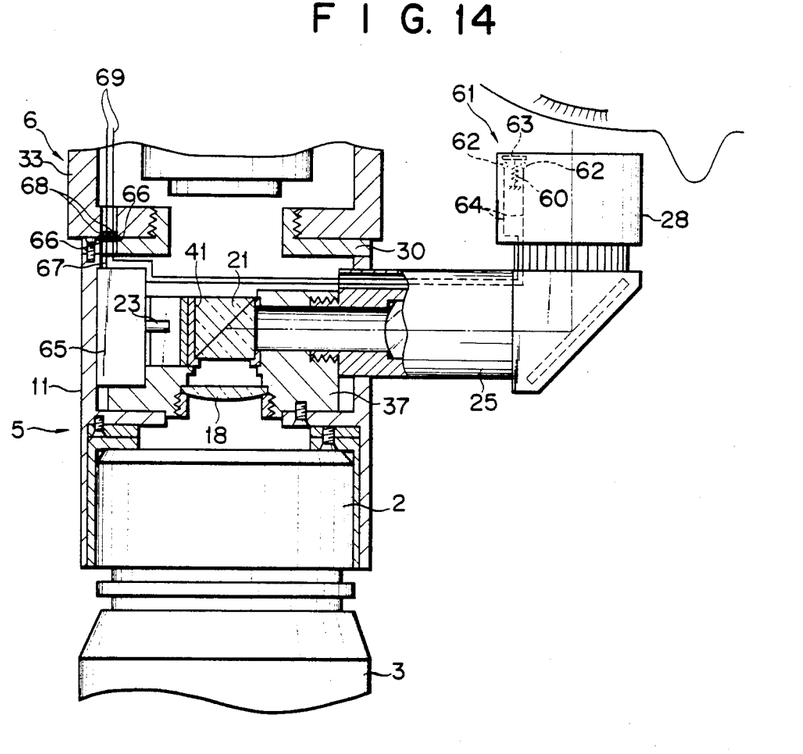
FIGS. 14 and 15 are respectively a longitudinal sectional view and a transversal sectional view showing a fourth embodiment of a connecting device for an endoscope according to the invention.
Figure 15:
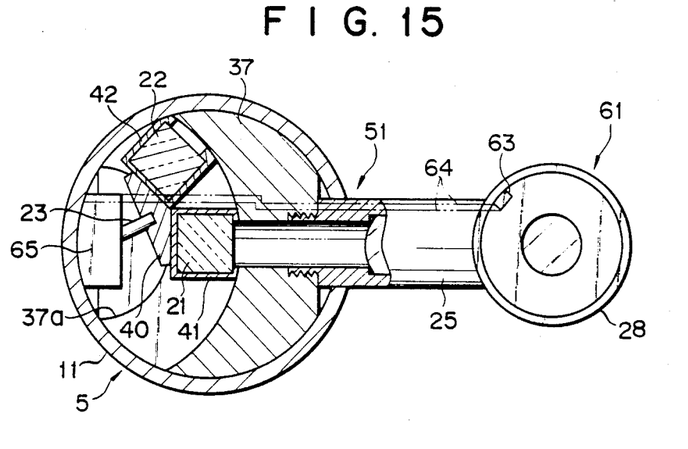

FIGS. 14 and 15 show a fourth embodiment of the invention, in which the switching of prisms is done automatically by electric drive means with the mounting and demounting of the still camera.

Here, a switch mechanism 61 is provided on the top of the eyepiece section 28 of connecting device 5. The switch mechanism 61 includes a pair of horizontally spaced-apart first contacts 62 and a contact piece 63 which is disposed to face these contacts and may be electrically connected thereto when urged. The contact piece 63 is biased away from the contacts 62 by a spring 60. When the still camera is mounted on the eyepiece section, the contact piece 63 is urged by the mount of the camera into contact with the contacts 62. The contacts 62 are connected to first lead wires 64 which are led along the peripheral wall of the light guide 25 into the body 11. One of these lead wires is connected to a coil of a rotary solenoid 65, which is mounted on the inner wall of the body 11 and is found between the body 11 and the arcuate surface 37a of the support 7. The operating rod 23 constitutes an operating shaft of the solenoid. The end of the operating rod 23 is secured to movable prism holder 40 as in the preceding embodiment. The other one of the pair lead wires is connected to one of second contacts 66 provided as a pair on a connecting member 30. The other one of the second contacts 66 is connected to a lead wire 67, which is in turn connected at the other end to the coil of the solenoid 65. The second contacts 66 are adapted to be brought into contact with respective third contacts 68 provided as a pair on the casing of the television camera 6. The third contacts 68 are connected to respective lead wires 69 leading to a power source (not shown) for the television camera 6.

With the construction as described above, when the still camera is mounted, the switch mechanism 61 is automatically closed. As a result, the solenoid 65 is excited to turn the operating rod 23 in the counterclockwise direction in FIG. 15, whereby the second prism 22 is brought to the position to face the light guide 25 in place of the first prism 21. When the still camera is removed from the eyepiece section, the switch mechanism is opened to de-energized the solenoid 65. Thus, the operating rod is turned in the opposite direction, bringing the first prism to the position to face the light guide 25.

In the third embodiment of the connecting device shown in FIGS. 8 to 12 and the fourth embodiment shown in FIGS. 14 and 15, like the first and second embodiments, the light splitting ratio may be readily changed when the still camera is mounted from the value when the camera is not mounted. Besides, the light splitting ratio can be changed automatically, which is very convenient for operation.

While the above embodiments have used prisms as the light splitter, it is also possible to use other light splitters such as half mirrors. Further, it is possible to use more than two light splitters. Further, while the above embodiments have used a prism with a light splitting ratio of 3:7 and a prism with a light splitting ratio of 5:5, this is by no means limitative, and it is possible to use any other suitable combination of light splitting ratios, for instance a ratio combination of 4:6 and 3:7 or 6:4 and 5:5.

What is claimed is:

1. A connecting apparatus for optically connecting an endoscope and a television camera and selectively optically connecting the endoscope to a still camera simultaneously with the optical connection between the endoscope and the television camera, comprising:
    a connecting device which connects the endoscope and the television camera in a state aligned to a first optical axis and is capable of connecting the still camera to it, including: an eyepiece section having a second optical axis crossing said first optical axis to define an optical path intersection point; supporting means movable located adjacent to said optical path intersection point; first and second light splitting members mounted on said supporting means, and first light splitting member having a light splitting ratio different from the light splitting ratio of said second light splitting member so that the first light splitting member guides more light to the television camera than does the second light splitting member; and driving means for moving said supporting means to selectively bring each of said first and second light splitting members to a position corresponding to the optical path intersection point and automatically moving said second light splitting member to said optical path intersection point when the still camera is mounted on said eyepiece section, said driving means including biasing means connected to said supporting means for urging said supporting means into a position with said first light splitting member located at said optical axis intersection point and moving means connected to said supporting means for overcoming the urging of said biasing means and moving said supporting means into a position with said second light splitting member located at said optical path intersection point, and moving means actuating means mounted on said eyepiece section for actuating said moving means when a still camera is mounted on said eyepiece and for deactuating said moving means when the still camera is removed from said eyepiece section so that said biasing means moves said first light splitting member back to said optical path intersection point;
    an engaging member provided on the eyepiece of the endscope to be engaged with the mount portion of the still camera, said moving means actuating means being connected to said engaging member; and means on the still camera for engaging said engaging member.

2. The connecting device according to claim 1, wherein said supporting means includes a cylindrical body connected at one end to the television camera and connected at the other end to the endoscope, and a light guide secured to said body and extending from said body, said eyepiece section being provided on the end of said light guide opposite said body, said light guide being coaxial with said second optical axis.

3. The connecting device according to claim 2, wherein said supporting means has a mounting groove, said first and second light splitting members being disposed in said mounting groove for movement therealong.

4. The connecting device according to claim 3, wherein said mounting groove is a straight groove, said first and second light splitting members being disposed in said straight mounting groove for movement therealong, and wherein said driving means includes an operating rod having one end projecting from the outer periphery of said cylindrical body and the other end connected to said first and second light splitting members, said operating rod being movable relative to said body.

5. The connecting device according to claim 3, wherein said mounting groove is an arcuate groove, and wherein said driving means includes a coupling member securing said first and second light splitting members to each other so that said first and second light splitting members are moved in unison with each other along said arcuate groove, and an operating rod having one end projecting from the outer periphery of said cylindrical body and the other end connected to said coupling member, said operating rod being pivotally 6. The connecting device according to claim 1, wherein said driving means includes a wire connected at one end to said light splitting members and led to said eyepiece section, said wire being pulled to move said light splitting members when the still camera is mounted on said eyepiece section.

7. The connecting device according to claim 1, wherein said first light splitting member leads 50% of incident light to the television camera and leads the remaining 50% of light to said eyepiece section, and said second light splitting member leads 30% of incident light to the television camera and the remaining 70% of light to said eyepiece section.

8. The connecting device according to claim 2, wherein said driving means includes a switch closed when the still camera is mounted on said eyepiece section and electric means electrically driven to move said light splitting members with the closure of said switch.

* * * * *